(12) United States Patent
Sollmann et al.

(10) Patent No.: US 12,202,237 B2
(45) Date of Patent: *Jan. 21, 2025

(54) ELASTIC FILM AND METHOD FOR PRODUCING AN ELASTIC LAYER MATERIAL

(71) Applicant: Nitto Advanced Film Gronau GmbH, Gronau (DE)

(72) Inventors: Henner Sollmann, Gronau (DE); Peer Brolund, Gronau (DE); Ralf Schwering, Steinfurt (DE)

(*) Notice: Subject to any disclaimer, the term of this patent is extended or adjusted under 35 U.S.C. 154(b) by 0 days.

This patent is subject to a terminal disclaimer.

(21) Appl. No.: 17/947,258

(22) Filed: Sep. 19, 2022

(65) Prior Publication Data

US 2023/0017363 A1    Jan. 19, 2023

Related U.S. Application Data

(63) Continuation of application No. 16/654,245, filed on Oct. 16, 2019, now Pat. No. 11,479,012.

(30) Foreign Application Priority Data

Oct. 17, 2018   (DE) ...................... 10 2018 125 746.5

(51) Int. Cl.
*B32B 3/24* (2006.01)
*B29D 7/01* (2006.01)
*B32B 3/26* (2006.01)
*A61F 13/49* (2006.01)

(52) U.S. Cl.
CPC ............. *B32B 3/266* (2013.01); *B29D 7/01* (2013.01); *A61F 13/4902* (2013.01); *B29C 2793/0045* (2013.01); *B32B 2307/51* (2013.01); *B32B 2307/732* (2013.01); *B32B 2555/02* (2013.01)

(58) Field of Classification Search
CPC .................................................... B32B 3/266
See application file for complete search history.

(56) References Cited

U.S. PATENT DOCUMENTS

| 5,336,554 A | 8/1994 | Knight |
| 7,083,837 B1 | 8/2006 | Varriano-Marston |
| 2007/0155900 A1 | 7/2007 | Chang et al. |
| 2012/0196060 A1 | 8/2012 | Hansen et al. |
| 2018/0126618 A1 | 5/2018 | Middlesworth et al. |

FOREIGN PATENT DOCUMENTS

| DE | 19647543 A1 | 5/1998 |
| EP | 1355604 B3 | 10/2003 |
| EP | 1598172 A1 | 11/2005 |
| WO | 01/39712 A1 | 6/2001 |

OTHER PUBLICATIONS

German Office Action dated Jun. 19, 2019 (with English translation of relevant parts).
ASTM Designation: D882-12 Standard Test Method for Tensile Properties of Thin Plastic Sheeting, downloaded Aug. 30, 2016.

*Primary Examiner* — William P Watkins, III
(74) *Attorney, Agent, or Firm* — Collard & Roe, P.C.

(57) ABSTRACT

An elastic film has a perforation formed by perforation holes that are elongated along a preferred expanding direction in the unexpanded state, wherein the ratio of the length of the perforation holes determined along the preferred expanding direction to a width of the perforation holes determined perpendicular thereto amounts to at least 3:2. The elongation at break along the preferred expanding direction is at least twice as high as the elongation at break determined perpendicular thereto along the width of the perforation holes.

14 Claims, 6 Drawing Sheets

ELASTIC FILM AND METHOD FOR PRODUCING AN ELASTIC LAYER MATERIAL

CROSS-REFERENCE TO RELATED APPLICATIONS

This application is a continuation of and claims priority under 35 U.S.C. 120 of U.S. patent application Ser. No. 16/654,245 filed on Oct. 16, 2019, which claims priority under 35 U.S.C. 119 of German Application No. 10 2018 125 746.5 filed on Oct. 17, 2018, the disclosures of each of which are herein incorporated by reference. A certified copy of priority German Patent Application No. 10 2018 125 746.5 is contained in parent U.S. patent application Ser. No. 16/654,245.

BACKGROUND OF THE INVENTION

The invention is directed to an elastic film with a perforation formed by perforation holes.

The elastic film is provided particularly for producing single-use hygiene articles such as baby diapers or incontinence articles for adults. The elastic film is usually laminated in a suitable manner with at least one cover layer of nonwoven to form a laminate with elastic recovery properties.

Baby diapers or incontinence articles for adults usually have a base body with a liquid-tight back wall, a liquid-permeable inner wall and an absorbent pad arranged therebetween. In order to hold the base body in the user's hip area, a back side and a front side of the base body are connected to one another laterally in the attached state, the leg openings for the user usually being provided below this lateral connection.

The laminate comprising the elastic film and at least one cover layer of nonwoven can be provided particularly for the lateral connection of a hygiene article of this kind. The laminate can be permanently and indissolubly connected to the base body to form a disposable diaper. Alternatively, the laminate can also be fastened in a suitable manner only at the front side or preferably the back side of the base body and can have closure means, for example, a hook material, at its opposite free end in order to form a Velcro-type closure particularly together with a corresponding mating surface (landing zone). Corresponding elements with a laminate having elastic recovery properties are also known in practice as diaper ears.

There are various specific requirements for the hygiene products described above. In view of the fact that they are disposable articles, it is desirable that production costs are as low as possible so that the individual components are to be formed using as little material as possible and in the simplest possible manner. On the other hand, it is also required that they be highly comfortable for the user and comfortable to wear. In particular, the hygiene articles described above must be adaptable to different body shapes and must also follow the movements of a user. The above-described hygiene articles must also be prevented from slipping or leaking. For this purpose, elastic films with extensive elasticity are usually used so that the required holding forces can be generated without unwanted constrictions.

To this end, the elastic film can have, for example, at least one elastic film layer of styrene block copolymer with the usual additives and auxiliaries.

However, in principle, other materials and blends are taken into consideration within the framework of the invention. The expression "elastic film" as used herein refers to a film which is expandable by at least 100% in at least one direction starting from an initial length without tearing, and after the tensile force is removed the remaining deformation is less than 25% of the initial length. However, conventional thermoplastic elastomers which are also suitable within the framework of the invention have an appreciably higher expandability and smaller permanent deformations in practice.

SUMMARY OF THE INVENTION

The present invention specifically proceeds from an elastic film with a perforation formed by perforation holes so as also to ensure good breathability through the perforation. It is precisely when applied in the manner described above by way of example as component part of a closure band of hygiene articles that such breathability is particularly advantageous for increasing wearing comfort and protecting the user's skin from perspiration and moisture through which skin irritation or sores could occur precisely during a continuous movement.

In principle, a perforation of this kind can be formed in different ways. A generic elastic film in which the perforation is formed by laser radiation is known from U.S. Pat. No. 5,336,554, the disclosure of which is herein incorporated by reference.

The present invention is also directed to a particular extent to a perforation formed in this way, which may also be referred to as laser perforation. A laser perforation is distinguished through specific features and is also clearly identifiable on the finished product in practice.

Through the use of a laser, the elastic film is melted, which usually results in a circular opening surrounded by a bulge with increased thickness. This bulge forms through the polymer material which is melted by the laser and which hardens again afterward. On the one hand, the bulge of polymer material which is first melted and then hardened is very uniform so that—in contrast to a mechanically produced perforation—there are few very pronounced local weak points, if any, which promote tearing. On the contrary, it may even be the case that the accumulation of material in the bulge results in a stabilization in a particularly advantageous manner. Accordingly, the weakening brought about by the production of the perforation in itself can be reduced to a slight extent in the case of laser perforation.

It is particularly noted in U.S. Pat. No. 5,336,554 that an improvement is even achieved over an unperforated film by the above-described perforation with respect to further tearing.

Further, a generic elastic film is also known from EP 1 598 172 A1.

Although comparatively good results can be achieved precisely with a laser perforation, the perforation leads to a deterioration compared to an unperforated film precisely with respect to maximum elongation at break.

In view of the foregoing, the present invention has the object of improving the mechanical characteristics of the elastic film and enabling a broader spectrum of application and greater comfort for a user.

Further, a method is also to be provided for producing a corresponding elastic layer material with at least the elastic film.

The subject matter of the invention and the solution to the above-stated object are an elastic film with a perforation formed by perforation holes, particularly laser perforation, wherein the perforation holes are elongated along a preferred expanding direction in an unexpanded state, wherein the ratio of the length of the perforation holes determined along the preferred expanding direction to the width of the perforation holes determined perpendicular thereto amounts to 3:2, and that the elongation at break along the preferred expanding direction is at least twice as high as the elongation at break determined perpendicular thereto along the width of the perforation holes.

According to the prior art, substantially round perforation holes are generated by means of laser. This is also due to the fact that the polymer material of the elastic film melts when impinged by the laser beam and retracts proceeding from the impingement point to form the bulge that is typical of a laser perforation and advantageous with respect to mechanical characteristics.

In view of the foregoing, however, the present invention provides an elongated shape of the perforation holes with an aspect ratio of at least 3:2. An elongated shape of this kind can be achieved in that, for the production of every perforation hole, an associated laser beam is moved in a relative motion over a length of at least 200 μm, for example, over the elastic film.

According to the invention, the perforation holes along the preferred expanding direction are elongated in the above-described manner. In the case of an elastic film, precisely in the cases of application described in the introductory part, it is known in advance in which direction an expansion takes place subsequently. According to the invention, it is also provided that the elongation at break along the preferred expanding direction is at least twice as high as the elongation at break determined perpendicular thereto along the width of the perforation holes. The elongation at break is given as a percentage proceeding from an initial length. Elongation at break is a conventional characteristic parameter of films and especially of elastic films. The present invention refers to the standard ASTM 882-12 with respect to the determination of elongation at break. In this regard, it should be taken into account that the elongation at break, in accordance with the conventional nomenclature, relates to the total length of a corresponding film sample and not only to the increase in length during an expansion.

In this connection, the present invention is based on the insight that, as a result of the perforation holes which are elongated along the preferred expansion direction, the elastic film is weakened to a lesser extent than is the case perpendicular to the preferred expanding direction. It is already clear from geometric considerations that the elastic film is weakened less through the elongated shape with respect to the preferred expanding direction. It could be intended, for example, to replace a wide strip of elastic film extending in expanding direction with a plurality of narrower strips, in which case a similar elastic behavior would be taken into account. Consequently, insofar as such strips are connected to one another perpendicular to the preferred expanding direction only by narrow strips, there would also only be a low strength and therefore also only a low elongation at break perpendicular to the preferred expanding direction.

The ratio between the length and width of the perforation holes in the unexpanded condition of the film amounts to at least 3:2 and can typically be between 3:2 and 4:1. As a result of melting by means of laser radiation, the individual perforation holes usually have a uniform oval shape with two axes of symmetry, particularly an approximately elliptical shape. According to a preferred configuration of the invention, the surface area of the perforation holes can amount to between 0.5 $mm^2$ and 1 $mm^2$, and the hole area percentage can amount to between 0.5% and 10%.

In principle, the elastic film can also be activated after the perforation is produced by an expansion or can be expanded in some other way during processing, wherein the ratio of 3:2 particularly to the characteristics of the elastic film prior to such an activation or in further expansion.

The perforation holes can be provided in the elastic film uniformly or in a pattern.

In particular, at least one strip provided with perforation holes and an unperforated strip can alternate with one another along the preferred expanding direction or perpendicular to the preferred expanding direction.

The thickness of the elastic film is typically between 15 μm and 70 μm, and the elastic film has at least one elastic film layer comprising a thermoplastic elastomer. Elastic polyolefins or styrene block copolymers such as styrene-butadiene-styrene block copolymer (SBS) and styrene-isoprene-styrene block copolymer (SIS), for example, are suitable for such an elastic film layer.

A $CO_2$ laser or Nd:YAG laser, in particular, may be considered as source for the laser radiation. In order to generate a plurality of perforation holes simultaneously, a beam splitting can preferably be carried out by means of corresponding optical devices. In order to form the individual perforation holes with the elongated shape according to the invention, the corresponding laser beams can, in principle, also be fanned out such that they impinge on the film in a line-shaped manner rather than in a substantially point-shaped manner. However, it is preferably provided that an associated laser beam impinges on the film in a substantially point-shaped or circle-shaped manner for generating each perforation hole and then, in order to generate the elongated shape, is moved over the film, which is easily possible by means of mirrors which are driven by piezoelectric means or by motor in some other manner.

In order to facilitate the generation of perforation holes by means of laser, the elastic film can also contain absorbent additions which are also referred to as laser additives. Corresponding additions may be advisable, particularly in thermoplastic olefin-based elastomers (TPE-O), to ensure a sufficient absorption of laser radiation.

In principle, the elastic film can also be configured as monofilm which then exclusively comprises the elastic film layer described above. Alternatively, a multilayer configuration is also possible. A film of this kind can be formed particularly by coextrusion.

With a multilayer configuration, a non-elastic or less elastic cover layer can also be provided in particular; however, the at least one elastic film layer brings about the required elastic recovery after the expansion. Non-elastic cover layers are known from the prior art and may be formed from polyolefins, for example. An elastic film of this kind has the advantage first that it can be processed more easily, and a blocking of the film in rolled-up state is also prevented.

The elongation at break along the preferred expanding direction preferably amounts to at least 600%, for example, between 700% and 1000%.

The elongation at break perpendicular to the preferred expanding direction is typically between 110% and 300%. In this regard, it must be taken into account that the elastic film must also be capable of sustaining loads to a certain extent perpendicular to the preferred expanding direction, particularly so that a permissible processing is also made possible. This applies particularly when, in accordance with a preferred configuration of the invention, the preferred expanding direction is oriented perpendicular to a production/processing direction.

During the processing of the film, tensile forces must be exerted solely for transporting the film along the processing direction, during which an excessive expansion and consequent lengthening must be avoided and tearing must also be prevented. A sufficient tensile strength is provided particularly when, during a typical expanding of the film along processing direction of 5% with respect to an initial length in the unloaded state, the tensile force amounts to at least 1.5 N/inch (Newtons per 2.54 cm film width), preferably at least 2.5 N/inch, for example, between 2.5 N/inch and 3 N/inch.

The production/processing direction is also referred to as machine direction MD so that the preferred expanding direction corresponds to the transverse direction CD.

The bulge existing around the perforation holes has an increased thickness, where the thickness may be greater than the actual film thickness by a factor of 2 to 4, for example. As a result of this, the specified thickness of the elastic film of typically between 15 µm and 70 µm at a distance from the perforations is to be determined where the elastic film remains extensively unaffected by the formation of the perforation holes by means of laser. The thickness of the bulge is preferably constant or approximately constant around the circumference of the individual perforation holes.

A further subject matter of the invention relates to a method for producing an elastic layer material, wherein an elastic film is guided along a production direction and a plurality of perforation holes is formed by means of laser radiation such that, to generate each perforation hole, an associated laser beam is moved over the elastic film over a length of at least 200 µm, preferably at least 300 µm, in a relative movement along a preferred expanding direction of the film, and the perforation holes accordingly obtain a shape that is elongated along the preferred expanding direction.

According to a preferred further development of the invention, it is provided that the preferred expanding direction extends perpendicular to the production direction along a transverse direction, wherein the elastic film is free from tensile forces in transverse direction during the generation of the perforation. Further, only low tensile forces are also usually provided along longitudinal direction during which the elastic film is typically expanded by less than 20%.

If, according to a variant of the invention, the elastic film has at least one non-elastic cover layer, an unwanted expansion in longitudinal direction through the usual web tension can also be ruled out during production.

During the production of the elastic layer material, the elastic film which is provided with the perforation can also be laminated with at least one cover layer comprising nonwoven, wherein a cover layer comprising nonwoven is provided in each instance in a particularly preferred manner on both sides of the elastic film.

Accordingly, it is preferably provided that the elastic film is provided with the described perforation before connecting to at least one cover layer. In principle, however, it is also conceivable to generate the perforation after the film is connected to at least one cover layer. A procedure of this kind may be advisable particularly when, as a result of the materials employed and/or due to laser-absorbent additions, the film absorbs the impinging laser radiation to a greater extent than a cover layer which comprises nonwoven and which is preferably not modified, or not substantially modified, by the laser irradiation. If a cover layer is only provided on one side of the film, the film can also be irradiated by means of the laser on the opposite side to generate the perforation in the film.

In principle, a laminate of this kind comprising elastic film and at least one cover layer of nonwoven can be formed in different ways.

In a particularly preferred manner, the elastic film and the at least one cover layer of nonwoven are connected to one another at connection surfaces or connection points by ultrasonic welding.

Corresponding laminates are known, for example, from EP 1 355 604 B3. According to this prior art, pores are formed directly at the connection surfaces or connection points in order to generate a breathability. However, corresponding pores represent weak points as concerns the tearing resistance of the laminate such that the laminate tears relatively quickly during an expansion and only comparatively low values can be achieved for elongation at break.

In view of the foregoing and within the framework of the invention, the ultrasonic welding is preferably carried out in such a way that no additional pores are generated at the connection surfaces or connection points. In particular, it can be provided that the elastic film is maintained as continuous material layer also at the connection surfaces or connection points in spite of the ultrasonic welding.

Accordingly, within the framework of an invention of this kind, in contrast to EP 1 355 604 B3, the generation of perforation is preferably functionally separate from the formation of the connection surfaces or connection points so that generally very good expansion properties and, in particular, also a high value for elongation at break can be achieved during an expansion along the preferred expansion direction.

If the at least one cover layer comprising nonwoven is connected substantially superficially to the elastic film within the framework of such an embodiment, it must also be accepted as regards mechanical characteristics that the perforation holes coincide or overlap with the connection surfaces or connection points in some areas.

According to a further development of the invention, it is provided that the elastic film expands along the preferred expansion direction after the perforation is generated and is connected to the at least one cover layer of nonwoven in the expanded state. Accordingly, a laminate is formed which is easily expandable after the tensile stress is eliminated, even when the nonwoven material itself is not elastic.

BRIEF DESCRIPTION OF THE DRAWINGS

Other objects and features of the invention will become apparent from the following detailed description considered in connection with the accompanying drawings. It is to be understood, however, that the drawings are designed as an illustration only and not as a definition of the limits of the invention.

In the drawings.

DETAILED DESCRIPTION OF THE EMBODIMENTS

Figure 1:
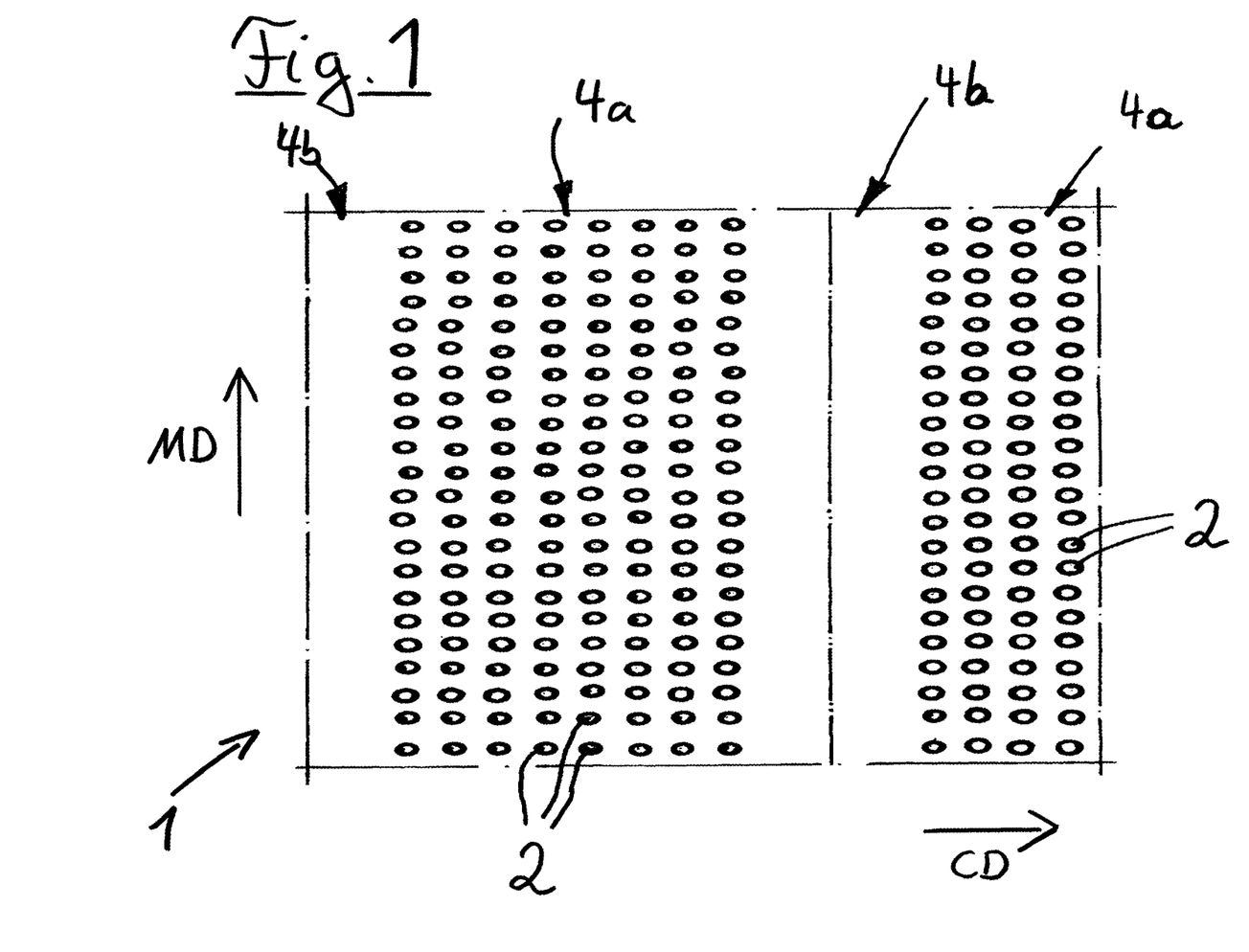
FIG. 1 shows a detail of an elastic film with a perforation formed by perforation holes.

FIG. 1 shows an elastic film 1 with a peroration formed by perforation holes 2 in an unexpanded state. The elastic film 1 has a production/processing direction, also referred to as machine direction MD, and a transverse direction CD perpendicular thereto.

As is also discernable from the figures described in the following, perforation holes 2 are generated by laser radiation. It can already be discerned from FIG. 1 that perforation holes 2 are elongated along the transverse direction CD in the depicted unexpanded state of the elastic film 1, this transverse direction CD also corresponding to a preferred expanding direction of the elastic film 1. The elongation at break determined in accordance with ASTM 882-12 along transverse direction CD as preferred expanding direction is at least twice as high as the elongation at break determined perpendicular thereto along machine direction MD.

The elongation at break determined along transverse direction CD preferably amounts to at least 600%, for example, between 750% and 1000%, in particular approximately 800%.

The elongation at break determined along machine direction MD is typically between 110% and 300%.

This highly anisotropic behavior is also a result of, and is promoted by, the elongated shape of the perforation holes 2. It can already be discerned from FIG. 1 that the perforation holes 2 which are elongated in transverse direction CD constitute a comparatively slight weakening with respect to this preferred expanding direction.

Figure 2:
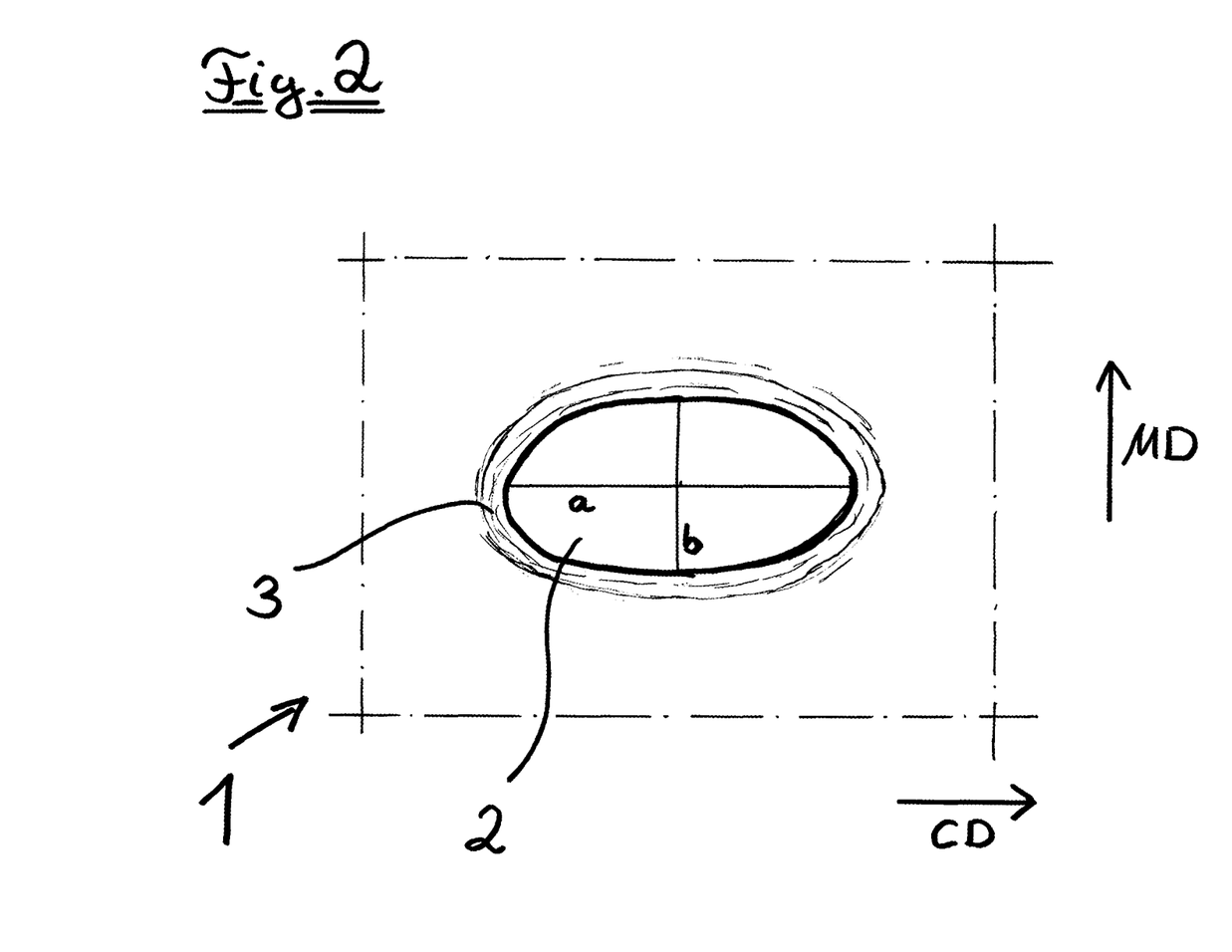
FIG. 2 shows a detailed view of an individual perforation hole in a top view.

In order to achieve the elongated shape of individual perforation holes 2 along transverse direction CD, an associated laser beam is moved over the elastic film 1 along a determined length of preferably at least 200 μm in a relative movement along transverse direction CD as preferred expanding direction of film 1 in order to generate each perforation hole 2 so that, as is shown in FIG. 2, the individual perforation holes 2 have an oval, particularly approximately elliptical, shape with a long axis a along transverse direction CD and a short axis b along machine direction MD as a result of the melting of the polymer material.

The ratio of the length of the perforation holes 2 determined along the long axis a to the width of the perforation holes 2 determined along the short axis b amounts to at least 3:2, particularly preferably 2:1. In particular, the ratio can be between 3:2 and 4:1.

The surface area of the individual perforation holes 2 is typically between 0.05 mm$^2$ and 1 mm$^2$, preferably between 0.1 mm$^2$ and 0.5 mm$^2$ and particularly preferably between 0.15 mm$^2$ and 0.3 mm$^2$.

The total hole area percentage of the perforation with respect to the total surface area of the elastic film 1 can be between 0.5% and 10% in particular.

The elastic film 1 has a sufficient breathability as a result of the perforation formed by perforation holes 2. According to the invention, the elastic expansion characteristics along transverse direction CD are influenced only slightly. In particular, a high elongation at break comparable to the characteristics of an unperforated film can be achieved, while an appreciable reduction in the elongation at break can be tolerated along machine direction MD.

Figure 3:
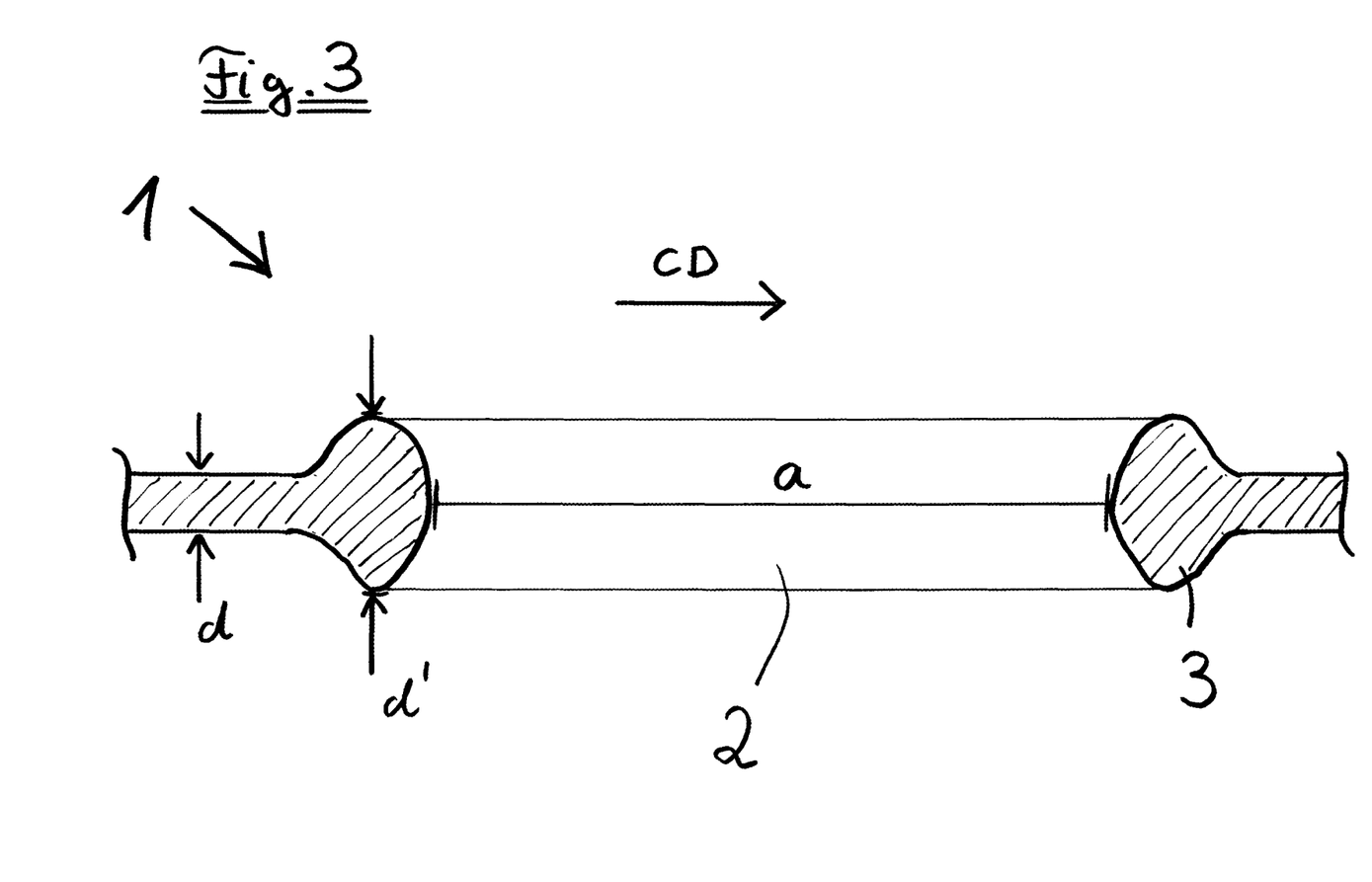
FIG. 3 shows a cross section through a perforation hole.

According to FIG. 3, this is also substantially due to the fact that the melted polymer material forms a bulge 3 around the actual perforation hole 2 when the perforation holes 2 are generated by means of laser. Proceeding from a thickness d of elastic film 1 of typically between 15 μm and 70 μm, the bulge 3 has a thickness d' which is increased at least by a factor of 2.

In the depicted embodiment example, the thickness d of the elastic film 1 outside the perforation 2 and the bulge 3 can amount to 50 μm, for example, while the thickness d' at the bulge 3 then amounts to 150 μm, for example.

Accordingly, bulge 3 contributes to a substantial strengthening and stabilization also resulting in a particularly uniform and smooth edge which can withstand tearing.

The perforation formed by the perforation holes 2 can be arranged uniformly over the entire elastic film 1. FIG. 1 shows an embodiment in which strips 4a provided with perforation holes 2 and unperforated strips 4b extending respectively along machine direction MD alternate along transverse direction CD as preferred expanding direction. As will be described more fully in the following, individual portions 5 extending along machine direction MD may be formed in that elastic film 1 is cut in the middle at the unperforated strips 4b, and these individual portions 5 can then be used to form an elastic layer material.

Figure 4A:
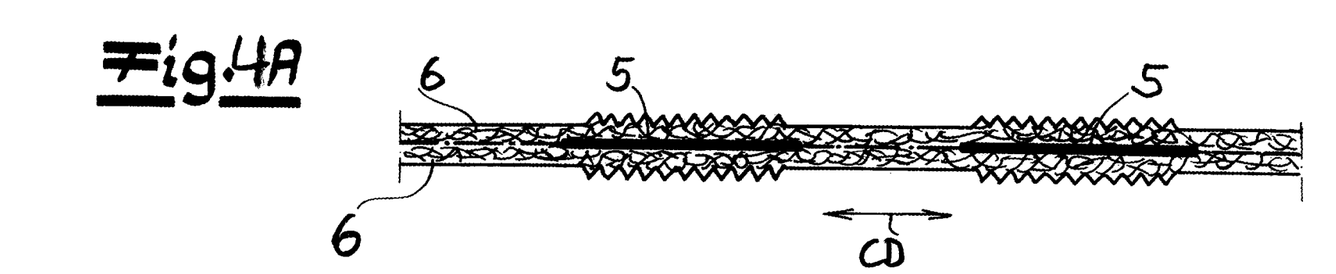
FIG. 4A shows a layer material with strips of elastic film in section.
Figure 4B:
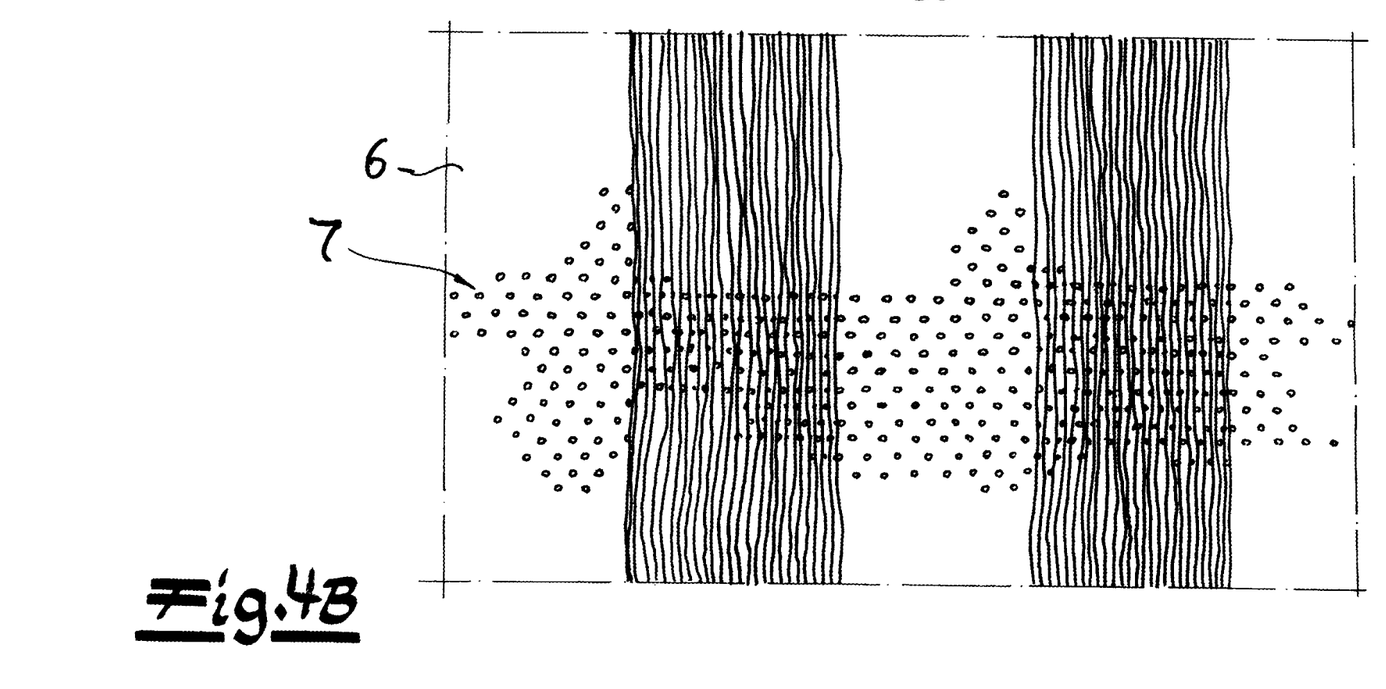
FIG. 4B shows the layer material according to FIG. 4A in a top view.
Figures 5A, 5B:
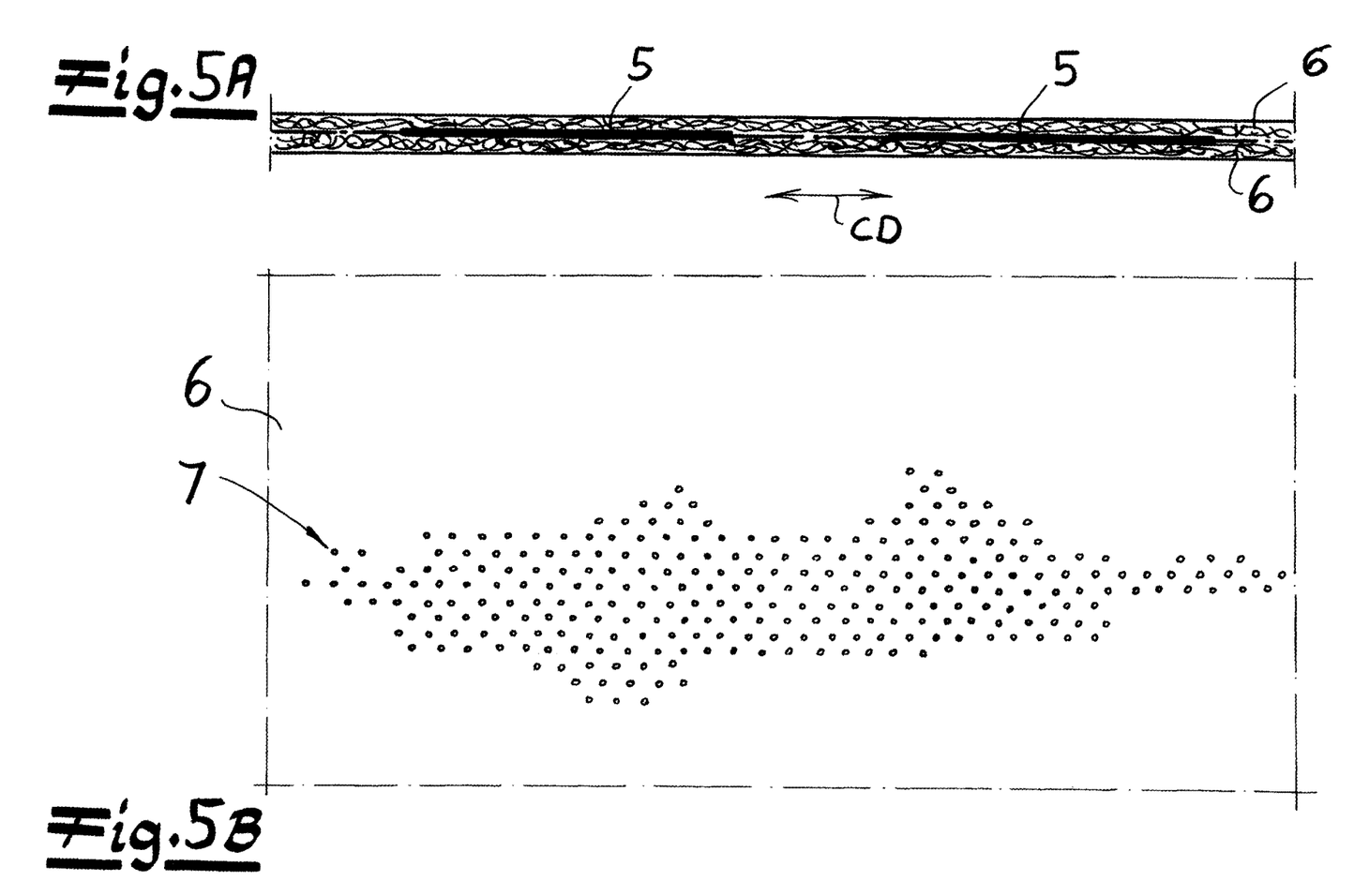
FIG. 5A and FIG. 5B show the material according to FIG. 4A and FIG. 4B in expanded condition.

In this connection, FIG. 4A shows a laminate with cover layers 6 of nonwoven and with portions 5 of film 1 therebetween. As was described above, portions 5 have the perforation formed by perforation holes 2, but the edges of portions 5 are not perforated and can accordingly be processed easily.

In a non-limiting manner, the elastic film 1 may be formed as a monofilm or in multiple layers as coextruded film, and the elastic film 1 has at least one elastic film layer which brings about the desired elastic recovery during an expansion.

It will be appreciated from the embodiment example shown in FIG. 4A that the cover layers 6 of nonwoven are pushed together in a wave-shaped manner along transverse direction CD at portions 5 of elastic film 1. This is a result of the fact that portions 5 of elastic film 1 are expanded along transverse direction CD when connected to cover layers 6 (stretch bonding), and the nonwoven material of cover layers 6 which still lies flat during the connection is compressed along transverse direction CD as a result of the elastic recovery of the portions 5 of elastic film 1 which are joined under tensile stress after the tensile stress is eliminated.

Individual closure bands can be cut out of the depicted laminate in such a way that an elastic central portion is formed at the individual closure bands in the area of the elastic film 1, while the adjoining ends of the cut portion are formed only from the two cover layers 6 that are connected to one another and these adjoining ends are not elastic.

In the depicted embodiment example, cover layers 6 and elastic film 1 are only partially connected to one another through a pattern of connection points 7 by means of ultrasonic welding. Compared to a lamination by means of adhesive, this has the advantage that no further material need be inserted into the laminate as a result of the ultrasonic welding, which may also be advantageous with respect to recycling or with respect to odor arising from the laminate.

Since the connection of the cover layers 6 to the elastic film 1 is carried out in the expanded state of the elastic film 1 supplied in the form of portions 5, the connection points 7 also lie closer together in the area of the elastic film 1 than in the rest of the areas in which the two cover layers 6 are connected to one another directly by connection points 7.

As a result of connecting the elastic film 1 to cover layers 6 in the expanded state, the laminate formed in this way is subsequently easily expandable during the joining process to the extent of the film 1. The mechanical characteristics are then substantially determined only by the elasticity of the elastic film 1.

Corresponding to the depiction in FIGS. 4A and 4B, FIGS. 5A and 5B show the laminate in an expanded state, wherein the cover layers 6 which were previously pushed together in a wave-shaped manner in unexpanded state in the area of the elastic film 1 again extend in a flat manner.

Figure 6:
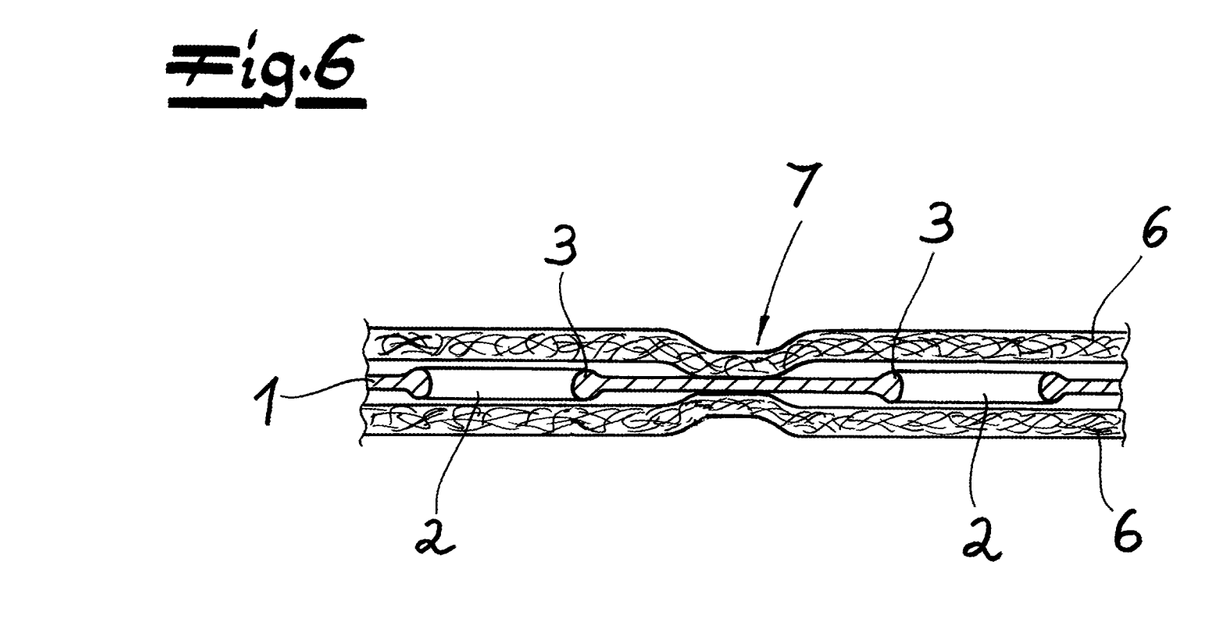
FIG. 6 shows a section through the layer material according to FIG. 4A in a detailed view.

In order to achieve the breathability of the laminate also in the area of the elastic film, the elastic film 1 is provided with perforation holes 2 as was described above. For the sake of clarity, the perforation holes 2 are shown in FIG. 6 at a distance from connection points 7. Connection points 7 can also intersect with perforation holes 2.

However, within the framework of the depicted embodiment form, it is key that the elastic film 1 is maintained at connection points 7 as continuous layer and that no additional pores or orifices are generated at that location. In a corresponding manner, no substantial material weakening results in this location, and only the perforation holes 2 formed by means of laser provide the required breathability.

As has already been described, a very good expandability can be achieved along transverse direction CD, as preferred expanding direction, through the shape of the perforation holes 2. According to FIG. 6, connection points 7 also do not lead to an unwanted weakening of the material.

Although only a few embodiments of the present invention have been shown and described, it is to be understood that many changes and modifications may be made thereunto without departing from the spirit and scope of the invention.

What is claimed is:

1. An elastic film with a perforation formed by laser-generated perforation holes that are elongated along a preferred expanding direction in an unexpanded state and have a bulge with an increased thickness (d') that runs around each of the perforation holes, wherein a ratio of a length of each of the perforation holes determined along the preferred expanding direction to a width of each of the perforation holes determined perpendicular thereto amounts to at least 3:2, and wherein an elongation at break along the preferred expanding direction is at least twice as high as the elongation at break determined perpendicular thereto along the width of the perforation holes.

2. The elastic film according to claim 1, wherein the perforation holes each have a surface area of between 0.05 mm$^2$ and 1 mm$^2$.

3. The elastic film according to claim 1, wherein a thickness (d) of the film amounts to between 15 μm and 70 μm.

4. The elastic film according to claim 1, wherein the elongation at break along the preferred expanding direction amounts to at least 600%.

5. The elastic film according to claim 1, wherein the elongation at break perpendicular to the preferred expanding direction is between 110% and 300%.

6. The elastic film according to claim 1, wherein the elastic film comprises at least one strip provided with the perforation holes, and an unperforated strip that alternates with the at least one strip with the perforation holes along the preferred expanding direction or perpendicular to the preferred expanding direction.

7. The elastic film according to claim 1, wherein the preferred expanding direction is oriented perpendicular to a production/processing direction.

8. The elastic film according to claim 1, wherein at least one elastic film layer of the elastic film is formed from styrene block copolymer.

9. The elastic film according to claim 1, wherein a hole area percentage of the perforation amounts to between 0.5% and 10%.

10. A method for producing an elastic layer material, comprising:
guiding an elastic film along a production direction, and creating a perforation in the elastic material by forming a plurality of perforation holes by means of laser radiation such that, to generate each perforation hole, an associated laser beam is moved over the elastic film over a length of at least 200 μm in a relative movement along a preferred expanding direction of the elastic film, and the perforation holes accordingly obtain a shape that is elongated along the preferred expanding direction and have a bulge of increased thickness that runs around each of the perforation holes, wherein a ratio of a length of each of the perforation holes determined along the preferred expanding direction to a width of each of the perforation holes determined perpendicular thereto amounts to at least 3:2, and wherein an elongation at break along the preferred expanding direction of at least twice as high as the elongation at break determined perpendicular thereto along the width of the perforation holes.

11. The method according to claim 10, wherein the preferred expanding direction extends perpendicular to the production direction along a transverse direction (CD), and the elastic film is free from tensile forces in the transverse direction (CD) during generation of the perforation.

12. The method according to claim 10, wherein the elastic film provided with the perforation is laminated with at least one cover layer of nonwoven.

13. The method according to claim 12, wherein the elastic film and the at least one cover layer of nonwoven are connected to one another at connection surfaces or connection points by ultrasonic welding.

14. The method according to claim 12, wherein the elastic film expands to an expanded state along the preferred expansion direction after the perforation is generated and is connected to the at least one cover layer of nonwoven in the expanded state.

* * * * *